(12) United States Patent
Riscoe et al.

(10) Patent No.: US 10,023,538 B2
(45) Date of Patent: Jul. 17, 2018

(54) COMPOUNDS, COMPOSITIONS AND ASSOCIATED METHODS COMPRISING 3-ARYL QUINOLINES

(71) Applicants: Oregon Health & Science University, Portland, OR (US); The United States of America as Represented by the Department of Veterans Affairs, Washington, DC (US)

(72) Inventors: Michael K. Riscoe, Tualatin, OR (US); Rolf W. Winter, Portland, OR (US); Sovitj Pou, Beaverton, OR (US); David J. Hinrichs, Sherwood, OR (US); Jane Xu Kelly, Lake Oswego, OR (US); Yuexin Li, Vancouver, WA (US); Aaron Nilsen, Portland, OR (US)

(73) Assignees: The United States of America as represented by the Department of Veterans Affairs, Washington, DC (US); Oregon Health and Science University, Portland, OR (US)

( * ) Notice: Subject to any disclaimer, the term of this patent is extended or adjusted under 35 U.S.C. 154(b) by 0 days.

(21) Appl. No.: 15/440,458

(22) Filed: Feb. 23, 2017

(65) Prior Publication Data
US 2018/0009760 A1 Jan. 11, 2018

Related U.S. Application Data

(63) Continuation of application No. 14/977,271, filed on Dec. 21, 2015, now abandoned, which is a continuation of application No. 14/371,870, filed as application No. PCT/US2013/021472 on Jan. 14, 2013, now Pat. No. 9,249,103.

(60) Provisional application No. 61/586,690, filed on Jan. 13, 2012.

(51) Int. Cl.
*C07D 215/46* (2006.01)
*C07D 401/12* (2006.01)
*A61K 31/47* (2006.01)

(52) U.S. Cl.
CPC ............ *C07D 215/46* (2013.01); *A61K 31/47* (2013.01); *C07D 401/12* (2013.01)

(58) Field of Classification Search
CPC ..... C07D 215/46; C07D 401/12; A61K 31/47
See application file for complete search history.

(56) References Cited

U.S. PATENT DOCUMENTS

| 4,652,441 | A | 3/1987 | Okada et al. |
| 4,675,189 | A | 6/1987 | Kent et al. |
| 4,677,191 | A | 6/1987 | Tanaka et al. |
| 4,728,721 | A | 3/1988 | Yamamoto et al. |
| 4,917,893 | A | 4/1990 | Okada et al. |
| 6,221,882 | B1 * | 4/2001 | Macfarlane ............ A61K 31/47 514/298 |
| 6,354,177 | B2 | 3/2002 | Peters |
| 6,354,711 | B1 * | 3/2002 | McCoy ............. A47G 23/0309 362/101 |
| 6,399,630 | B1 * | 6/2002 | Macfarlane ............ A61K 31/47 514/298 |
| 6,521,637 | B2 * | 2/2003 | Macfarlane ............ A61K 31/47 514/298 |
| 9,249,103 | B2 * | 2/2016 | Riscoe .................... A61K 31/47 |
| 2003/0232856 | A1 | 12/2003 | Macfarlane |

FOREIGN PATENT DOCUMENTS

| DE | 683 692 | 11/1939 |
| WO | WO 2000/076982 | 12/2000 |
| WO | WO 2008/064011 | 5/2008 |
| WO | WO 2010/059633 | 5/2010 |

OTHER PUBLICATIONS

Ramazani, Int J Pharma and Bio Sciences, vol. 2(2), 2011, B122-13131. (Year: 2011).*
Drake, CA40:29306, abstract only of J Am Chem Soc, vol. 68, p. 1208-1213, 1946. (Year: 1946).*
Andersag. "Antimalarials from the group of halogen-substituted quinoline compounds," *Chem Reports*, pp. 499-507 (1948) (with English translation).
Berge, et al. "Pharmaceutical salts." *Journal of Pharmaceutical Sciences* 66, No. 1 (1977): 1-19.
Childs, et al. "Comparison of in vitro and in vivo antimalarialactivities of g-phenanthrenecarbinols." *Annals of Tropical Medicine & Parasitology* 78, No. 1 (1984): 13-20.
Drake, et al. "Synthetic Antimalarials. The Preparation of Certain 4-Aminoquinolines1." *Journal of the American Chemical Society* 68, No. 7 (1946): 1208-1213.
Extended European Search Report dated Jun. 9, 2015 by the European Patent Office in European application No. 13735565.7 (5 pages).
Hart, et al. "Trace amine-associated receptor agonists: synthesis and evaluation of thyronamines and related analogues." *Journal of Medicinal Chemistry* 49, No. 3 (2006): 1101-1112.

(Continued)

*Primary Examiner* — D Margaret M Seaman
(74) *Attorney, Agent, or Firm* — Klarquist Sparkman, LLP

(57) ABSTRACT

Compounds, compositions and methods useful for treating infectious diseases are provided. In particular, 3-aryl quinoline compounds, their synthesis, pharmaceutical compositions thereof and methods of treating infectious diseases such as malaria, are disclosed.

9 Claims, No Drawings

(56) References Cited

OTHER PUBLICATIONS

International Report on Preliminary Patentability dated Jul. 15, 2014 in International Application No. PCT/US2013/021472.
International Search Report and Written Opinion dated May 9, 2013 by the Korean Intellectual Property Office acting as ISA in International Application No. PCT/US2013/021472.
Kelly, et al. "Discovery of dual function acridones as a new antimalarial chemotype." *Nature* 459. No. 7244 (2009): 270.
Kelly, et al. "Optimization of xanthones for antimalarial activity: the 3, 6-bis-ω-diethylaminoalkoxyxanthone series." *Antimicrobial Agents and Chemotherapy* 46, No. 1 (2002): 144-150.
Kelly, et al. "The kinetics of uptake and accumulation of 3, 6-bis-ω-diethylamino-amyloxyxanthone by the human malaria parasite *Plasmodium falciparum*." *Molecular and Biochemical Parasitology* 123, No. 1 (2002): 47-54.
Macfarlane, et al. "Antagonism of immunostimulatory CpG-oligodeoxynucleotides by quinacrine, chloroquine, and structurally related compounds." *The Journal of Immunology* 160, No. 3 (1998): 1122-1131.†.
Michel, et al. "The effect of site of administration in the gastrointestinal tract on the absorption of insulin from nanocapsules in diabetic rats." *Journal of Pharmacy and Pharmacology* 43, No. 1 (1991): 1-5.
Mphahlele, et al. "2-Aryl-4-chloro-3-iodoquinolines as substrates for the synthesis of 2, 3-diaryl-4-methoxyquinolines." *Journal of Chemical Research* 2008, No. 8 (2008): 437-440.
Pisciotta, et al. "The role of neutral lipid nanospheres in Plasmodium falciparum haem crystallization." *Biochemical Journal* 402, No. 1. (2007): 197-204.
Pou, et al. "Sontochin as a guide to the development of drugs against chloroquine-resistant malaria." *Antimicrobial Agents and Chemotherapy* 56, No. 7 (2012): 3475-3480.
Ramazani, et al. "In Silica Analysis and Develipment of Anti-Malarial Compounds Against Dihydroorotate Dehydrogenase Using Chembioinformatic Tools," *International Journal of Pharma and Bio Sciences* 2, No. 2 (2011): 122-131.
Smilkstein, et al. "Simple and inexpensive fluorescence-based technique for high-throughput antimalarial drug screening." *Antimicrobial Agents and Chemotherapy* 48, No. 5 (2004): 1803-1806.
Svensson, et al. "The design and bioactivation of presystemically stable prodrugs." *Drug Metabolism Reviews* 19, No. 2 (1988): 165-194.
Traebert, et al. "Inhibition of hERG K+ currents by antimalarial drugs in stably transfected HEK293 cells." *European Journal of Pharmacology* 484, No. 1 (2004): 41-48.
Wiselogle FY (ed). 1946. A survey of antimalarial drugs, 1941-1945. J.W. Edwards, Ann Arbor, MI, pp. 1145, 1152 (3 pages)††.

* cited by examiner

COMPOUNDS, COMPOSITIONS AND ASSOCIATED METHODS COMPRISING 3-ARYL QUINOLINES

ACKNOWLEDGEMENT OF GOVERNMENT SUPPORT

This invention was made with U.S. government support under the Merit Review Grant awarded by the Department of Veterans Affairs, and Contract Number RC1 AI087011 awarded by the National Institutes of Health. The U.S. government has certain rights in this invention.

TECHNICAL FIELD

This disclosure relates to compounds and methods useful in the treatment of infectious disease. More specifically, the disclosure relates to compounds, pharmaceutical compositions, and methods comprising 3-aryl quinoline which are useful in the treatment of malaria.

BACKGROUND

Malaria remains one of the deadliest diseases in the world today, as it has been for thousands of years. For each of the one million people killed by malaria each year, hundreds of millions more suffer from severe illness. The impact of malaria is particularly devastating in sub-Saharan Africa where its victims are primarily young children and pregnant women.

This situation is worsened by the growing emergence of *Plasmodium* parasites that are resistant to multiple drugs. The list of drugs that are losing potency against malaria includes the quinolines, such as chloroquine, quinine, and mefloquine; the antifolates, such as pyrimethamine and sulfadoxine; and the anti-respiratory combination of atovaquone and proguanil.

The present disclosure provides compounds, compositions and methods comprising 3-aryl quinolines that are effective against malaria infection, including malarial strains that have developed resistance to currently available drugs.

DETAILED DESCRIPTION

The present disclosure provides compounds, compositions, and methods of synthesizing 3-aryl quinolines that are effective against malaria infection, including malarial strains that have developed drug resistance. Also disclosed are methods of using the described compositions to treat parasitic diseases including those caused by infection with strains of drug-resistant malaria parasites.

I. Definitions

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as $R_1$, $X_1$, $X_2$, $X_3$, $X_4$, $X_5$, and n used throughout the disclosure are the same variables as previously defined unless stated to the contrary.

"Administration of" and "administering a" compound refers to providing a compound, a prodrug of a compound, or a pharmaceutical composition comprising a compound as described herein. The compound or composition can be administered by another person to the subject or it can be self-administered by the subject.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms ($C_{1-6}$ alkyl). The term "alkyl" also includes cycloalkyl. The alkyl group may be a "substituted alkyl" wherein one or more hydrogen atoms are substituted with a substituent such as halogen, cycloalkyl, alkoxy, amino, hydroxyl, aryl, or carboxyl.

The term "alkoxy" refers to an alkyl group attached to an oxygen atom to form an ether. The alkoxy group may be a "substituted alkoxy" wherein one or more hydrogen atoms are substituted with a substituent such as halogen, cycloalkyl, alkoxy, amino, hydroxyl, aryl, or carboxyl.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "aryl" refers to any carbon-based aromatic group including, but not limited to, benzene, naphthalene, phenyl, and oxazole. The term "aryl" also includes heteroaryl, which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ether, ketone, aldehyde, hydroxy, carboxylic acid, cyano, amido, haloalkyl, haloalkoxy, or alkoxy, or the aryl group can be unsubstituted.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, and cyclohexyl. The term "heterocycloalkyl group" is a cycloalkyl group as defined above where at least one of the carbon atoms of the ring is substituted with a heteroatom such as nitrogen, oxygen, sulfur, or phosphorous.

"Derivative" refers to a compound or portion of a compound that is derived from or is theoretically derivable from a parent compound.

"Equipotency" refers to the capacity of the inventive compounds disclosed herein to inhibit the growth of parasites, such as drug-resistant *Plasmodium* parasites, with roughly the same power or capacity (e.g., within a range of 2 to 3-fold), regardless of the level of intrinsic resistance to chloroquine, quinine, or other antimalarial agents.

The terms "halogenated alkyl" or "haloalkyl group" refer to an alkyl group as defined above with one or more hydrogen atoms present on these groups substituted with a halogen (F, Cl, Br, I). For example, a halomethyl group is a methyl group (—CH3) with one or more halogens substituted. A halomethyl group may include di- and tri-substituted halogens such as a trifluoromethyl group. A halogenated ether refers to a group with one or more hydrogen atoms present on an ether, such as a methyl ether (—OCH$_3$), substituted with one or more halogens. A halogenated ether may also be termed "halomethoxy" and this general term includes mono, di- and tri-substituted halogens on the ether. For example, a trifluoromethyl ether has a formula of —OCF$_3$ and may interchangably be referred to as "trifluoromethoxy."

"Heterocycle" means any optionally substituted saturated, unsaturated or aromatic cyclic moiety wherein said cyclic moiety contains at least one heteroatom selected from at least one of oxygen (O), sulfur (S), phosphorus (P) or nitrogen (N). Heterocycles may be monocyclic or polycyclic rings. Exemplary substituents include halogen, alkyl, halogenated $C_{1-6}$ alkyl, alkoxy, halogenated $C_{1-6}$ alkoxy, amino, amidino, amido, azido, cyano, guanidino, hydroxyl, nitro, nitroso, urea, OS(O)$_2$R, OS(O)$_2$OR, S(O)$_2$OR, S(O)$_{0-2}$R, or C(O)OR wherein R may be H, alkyl, aryl or any 3 to 10 membered heterocycle; OP(O)OR$_1$OR$_2$, P(O)OR$_1$OR$_2$, SO$_2$, NR$_1$R$_2$, NR$_1$SO$_2$R$_2$, C(R$_1$)NR$_2$, C(R$_1$)NOR$_2$, wherein R$_1$ and R$_2$ may be independently H, alkyl, aryl or 3 to 10 membered heterocycle; NR$_1$C(O)R$_2$, NR$_1$C(O)OR$_2$, NR$_3$C(O)NR$_2$R$_1$, C(O)NR$_1$R$_2$, OC(O)NR$_1$R$_2$, wherein R$_1$, R$_2$ and R$_3$ are each independently selected from H, alkyl, aryl or 3 to 10 membered heterocycle, or R$_1$ and R$_2$ are taken together with the atoms to which they are attached to form a 3 to 10 membered heterocycle.

Exemplary substituents of a heterocycle include halogen (Br, Cl, I or F), cyano, nitro, oxo, amino, alkyl (e.g., CH$_3$, C$_2$H$_5$, isopropyl, etc.); alkoxy (e.g., OCH$_3$, OC$_2$H$_5$, etc.); halogenated alkyl (e.g., CF$_3$, CHF$_2$, etc.); halogenated alkoxy (e.g., OCF$_3$, OC$_2$F$_5$, etc.); COOH, COO-alkyl, CO-alkyl, alkyl-S (e.g., CH$_3$S, C$_2$H$_5$S, etc.); halogenated alkyl —S(e.g., CF$_3$S, C$_2$F$_5$S, etc.); benzyloxy and pyrazolyl.

Exemplary heterocycles include, but are not limited to, azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

"Inhibiting" (which is inclusive of "treating") refers to inhibiting the development of a disease or condition, for example, in a subject who is at risk for a disease such as malaria, including malarial disease caused by chloroquine-resistant malaria parasites and/or multidrug-resistant malaria parasites. "Inhibiting" also refers to any quantitative or qualitative reduction, including prevention of infection or complete killing, of an invading organism relative to a control.

The terms "treatment", "treat" and "treating" refer to a therapeutic intervention that ameliorates a sign or symptom of a disease or pathological condition after it has begun to develop. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

A "prophylactic" treatment is a treatment administered to a subject who does not exhibit signs of a disease or exhibits only early signs, for the purpose of decreasing the risk of developing pathology.

"Coadminister" means that each of at least two compounds are administered during a time frame wherein the respective periods of biological activity overlap. Thus, the term includes sequential as well as coextensive administration of two or more drug compounds.

"Multidrug-resistant" or "drug-resistant" refers to malaria, or the parasites causing malaria, that have developed resistance to treatment by at least one therapeutic agent historically administered to treat malaria. For example, there are multidrug-resistant strains of Plasmodium falciparum that harbor high-level resistance to chloroquine, quinine, mefloquine, pyrimethamine, sulfadoxine and atovaquone, among others.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. Optionally substituted alkyl groups include haloalkyl groups, such as fluoroalkyl groups, including, without limitation, trifluoromethyl groups, trifluoromethyl ethers, and 1,1,1-triflouroethyl ethers.

"Optional" or "optionally" means that the subsequently described event or circumstance can but need not occur, and that the description includes instances where said event or circumstance occurs and instances where it does not.

The terms "pharmaceutically acceptable salt" or "pharmacologically acceptable salt" refers to salts prepared by conventional means, and include basic salts of inorganic and organic acids, such as hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid.

"Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

These salts may be prepared by standard procedures, for example by reaction of the free acid with a suitable organic or inorganic base. Any chemical compound recited in this specification may alternatively be administered as a pharmaceutically acceptable salt thereof.

"Pharmaceutically acceptable salts" are also inclusive of the free acid, base, and zwitterionic forms. Descriptions of exemplary pharmaceutically acceptable salts can be found in Stahl and Wermuth, Eds., Handbook of Pharmaceutical Salts; Properties, Selection and Use, Wiley VCH (2008). When compounds disclosed herein include an acidic function such as a carboxy group, then suitable pharmaceutically acceptable cation pairs for the carboxy group are well known to those skilled in the art and include alkaline, alkaline earth, ammonium, and quaternary ammonium cations. Such salts are known to those of skill in the art. For additional examples of "pharmacologically acceptable salts," see Berge et al., J. Pharm. Sci. 66:1 (1977).

"Saturated or unsaturated" includes substituents saturated with hydrogens, substituents completely unsaturated with hydrogens and substituents partially saturated with hydrogens.

The term "subject" includes both human and veterinary subjects.

A "therapeutically effective amount" refers to a quantity of a specified agent sufficient to achieve a desired effect in a subject being treated with that agent. For example, this may be the amount of a compound disclosed herein useful in treating drug-resistant malaria in a subject. Ideally, a therapeutically effective amount of an agent is an amount sufficient to inhibit or treat the disease without causing substantial toxicity in the subject. The therapeutically effective amount of an agent will be dependent on the subject being treated, the severity of the affliction, and the manner of administration of the therapeutic composition. Methods of determining a therapeutically effective amount of the disclosed compound sufficient to achieve a desired effect in a subject infected with a malaria parasite will be understood by those of skill in the art in light of this disclosure.

References cited throughout this disclosure, including journal articles and patents, are herein incorporated by reference.

II. Compounds and Methods of Synthesis

In certain embodiments, compounds according to the present description are described herein in reference to Formula (I), Formula (II), and Formula (III). In addition, examples of specific compounds according to the present description are provided herein.

In particular embodiments, compounds according to the present description include compounds having the structure shown below in Formula (I):

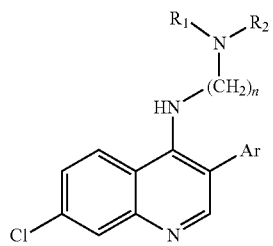

Formula (I)

In the compounds of Formula (I), the group labeled Ar may be any aryl group including a heteroaryl, substituted aryl, substituted heteroaryl, biaryl, heterobiaryl, substituted biaryl, substituted heterobiaryl, substituted diarylether, substituted heterodiaryl ether, benzophenone, substituted benzophenone, diphenylamine, substituted diphenylamine, heterodiphenylamine, and substituted heterodiphenylamine.

The groups labeled $R_1$ and $R_2$ may be independently selected from at least one of H, alkyl, cycloalkyl, or hydroxyl. In certain embodiments, $R_1$ and $R_2$ are connected to one another via a substituted or unsubstituted heterocyclic ring system such as a piperidine, pyrrolidine, or piperazine. In the compounds of Formula (I), n represents any integer from 1 to 5 inclusive. In some embodiments, n=3. An example of a structure of Formula (I) is Compound 5.

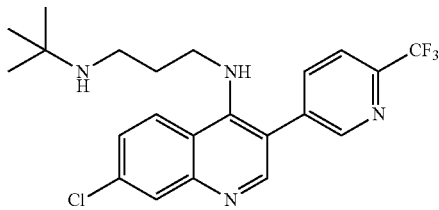

Compound 5

In other embodiments, compounds according to the present description include compounds having the structure shown in Formula (II)

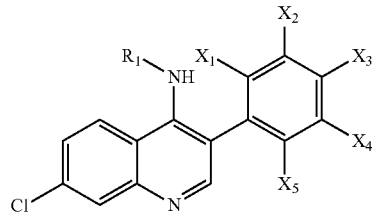

Formula (II)

In the compounds of Formula (II), $R_1$ is a substituted alkyl and $X_1$, $X_2$, $X_3$, $X_4$, and $X_5$ are independently selected from at least one of H, halo, alkoxy, ether, alkyl, substituted alkyl, alkyl ether, haloalkyl, haloalkyl ether, aryl, substituted aryl, aryl ether, substituted aryl ether, aryl amine, 5-member heterocycle, 6-member heterocycle, amino, benzylic amide, alkoxy, cyano, morpholinyl, N-ethyl morpholinyl, or carboxyl. In still further examples of the compounds of Formula (II) R1 may be selected from N-isobutylpropanamino, N-isobutylethanamino, N,N-d iethylpropanamino, N—N-diethyl-(4-methyl)butanamino, and 2-(2-piperidinyl) ethyl. Examples of compounds of formula (II) include:

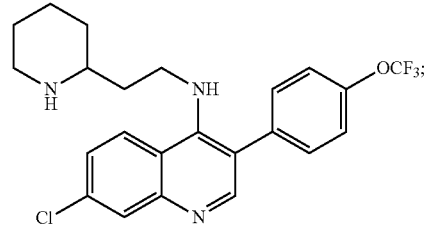

Compound 22

Compound 23

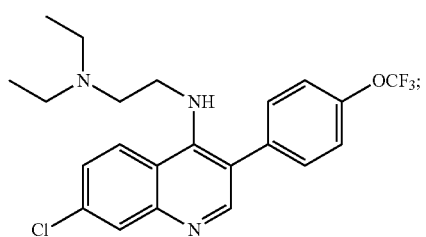

Compound 24

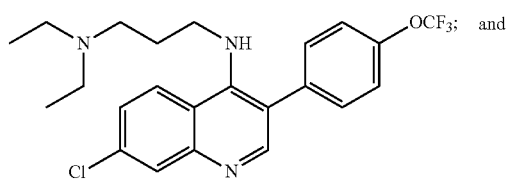
and

Compound 25

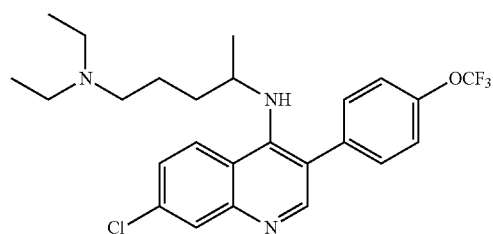

In further embodiments, compounds according to the present description include compounds having the structure shown in Formula (III).

Formula (III)

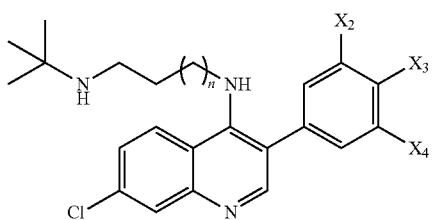

In the compounds of Formula (III) n is an integer equal to 2 or 3. $X_2$, $X_3$, and $X_4$ are independently H, halo, halomethyl, halomethoxy, dihalomethoxy, trihalomethoxy, haloethoxy, 1,1,1-trihaloethoxy, phenyl, phenyl ether, halomethoxy substituted phenyl, halomethoxy substituted phenyl ether, trihalomethoxy substituted phenyl ether, dimethylamino, cyano, morpholinyl, or ethyl-N-morpholine. Examples of compounds of formula (III) include Compound 1

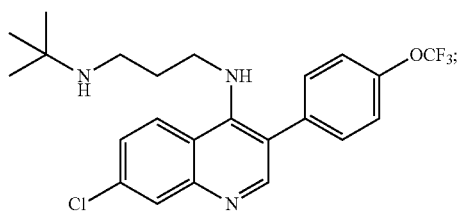

Compound 2

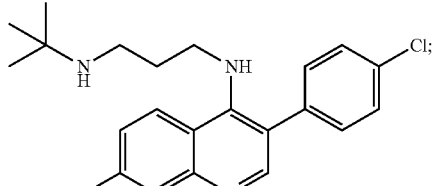

Compound 3

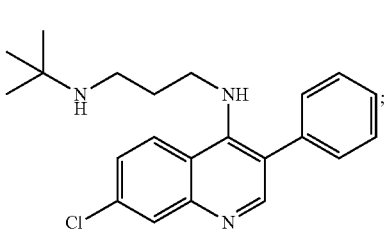

Compound 4

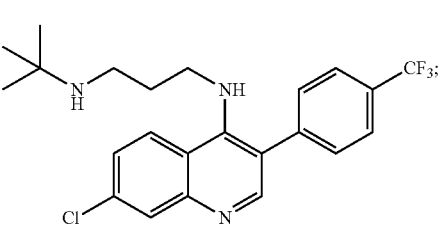

Compound 6

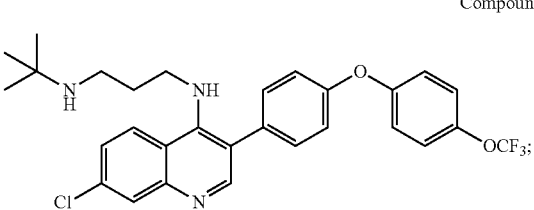

Compound 7

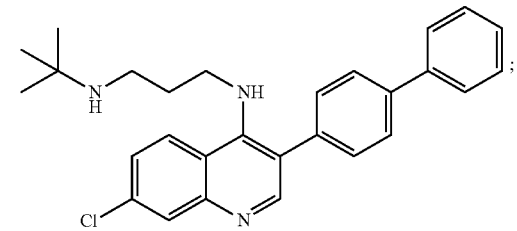

Compound 8

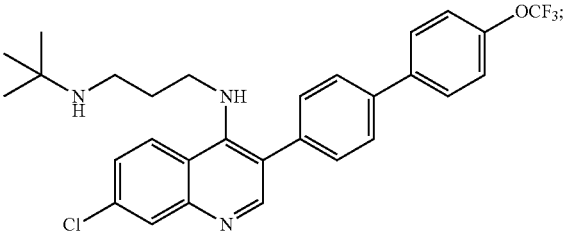

Compound 10

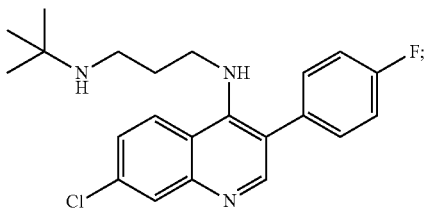

Compound 11

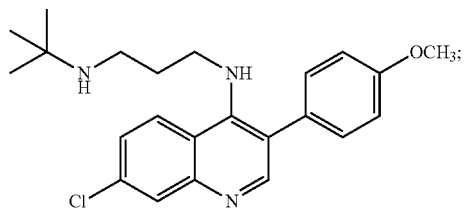

Compound 12

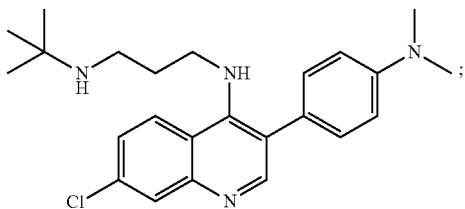

Compound 13

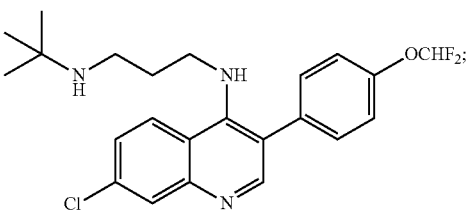

Compound 14

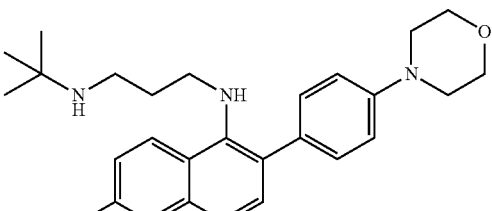

Compound 15

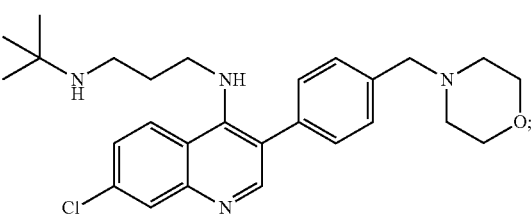

Compound 16

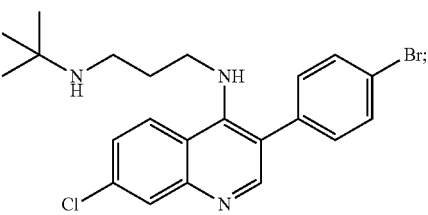

Compound 17

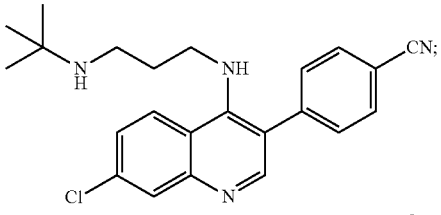

Compound 18

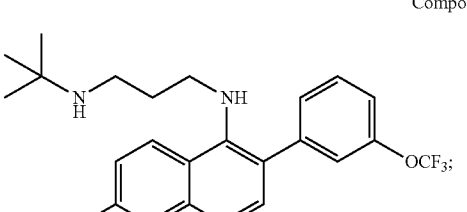

Compound 19

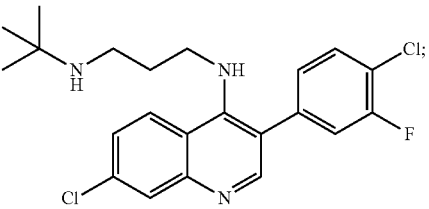

Compound 20

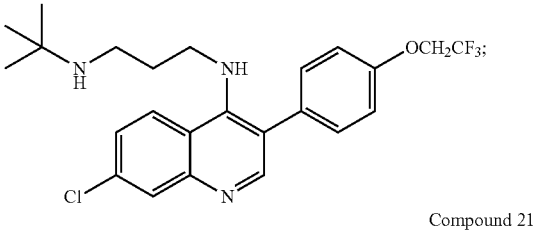

Compound 21

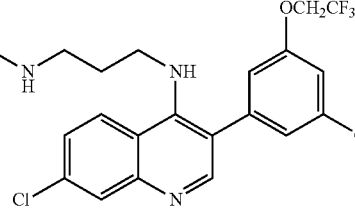

and

Compound 26

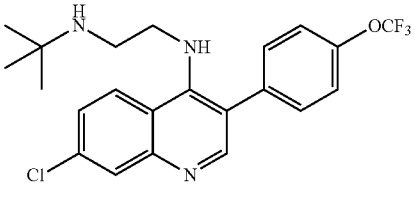

A prodrug is an active or inactive compound that is modified chemically through an in vivo physiological action, such as hydrolysis or metabolism, into an active compound following administration of the prodrug to a subject. The suitability and techniques involved in making and using prodrugs are well known by those skilled in the art. For a general discussion of prodrugs involving esters see Svensson and Tunek, Drug Metabolism Reviews 165 (1988), and Bundgaard, Design of Prodrugs, Elsevier (1985).

The term "prodrug" also is intended to include any covalently bonded carriers that release an active parent drug of the present invention in vivo when the prodrug is administered to a subject. The compounds and compositions disclosed herein may be delivered in prodrug form. Thus, also contemplated are prodrugs of the presently disclosed compounds, methods of delivering prodrugs and compositions containing such prodrugs.

Prodrugs of the disclosed compounds may be prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. For example, a prodrug may be a lower alkyl phosphonate ester, such as a methyleno phosphonate ester or an isopropyl phosphonate ester.

Protected derivatives of the disclosed compounds also are contemplated. A variety of suitable protecting groups for use with the disclosed compounds are described. Other conventional protecting groups can be selected by those of skill in the art, and/or in consultation with Greene and Wuts, Protective Groups in Organic Synthesis; 3rd Ed.; John Wiley & Sons, New York, 1999.

In general, protecting groups are removed under conditions which will not affect the remaining portion of the molecule. These methods are well known in the art and include, for example, acid hydrolysis and hydrogenolysis. One exemplary method involves the removal of an ester moiety, such as cleavage of a phosphonate ester using Lewis acidic conditions, such as in TMS-Br mediated ester cleavage to yield the free phosphonate.

A second exemplary method of removing a protecting group involves removal of a benzyl group by hydrogenolysis utilizing palladium on carbon in a suitable solvent system such as an alcohol or acetic acid, or mixtures thereof. A t-butoxy-based group, including a t-butoxycarbonyl protecting group, may be removed utilizing an inorganic or organic acid, such as HCl or trifluoroacetic acid, in a suitable solvent system, such as water, dioxane and/or methylene chloride.

Another exemplary protecting group, suitable for protecting amino and hydroxyl functions, is trityl. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Embodiments of the compounds disclosed herein include one or more asymmetric centers; thus, these compounds may exist in different stereoisomeric forms. Accordingly, compounds and compositions may be provided as individual pure enantiomers or as stereoisomeric mixtures, including racemic mixtures. In certain embodiments, the compounds disclosed herein may be synthesized in or are purified to be in a substantially enantiopure form, such as in a 90% enantiomeric excess, a 95% enantiomeric excess, a 97% enantiomeric excess or even in greater than a 99% enantiomeric excess, such as in enantiopure form.

Synthesis of Exemplary 3-Aryl Quinolines

The compounds described herein may be prepared in a variety of ways known to one skilled in the art of organic synthesis. For example, the compounds can be synthesized using the methods as hereinafter described below, together with synthetic methods known in the art of synthetic organic chemistry or variations thereon as appreciated by those skilled in the art. In addition, compounds according to the present description can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $_1$H or $_{13}$C NMR), infrared spectroscopy, spectrophotometry (e.g., UV-visible), mass spectrometry, or by chromatography such as high performance liquid chromatograpy (HPLC) or thin layer chromatography.

One embodiment of a scheme for the synthesis of Compound 1 is shown herein as Scheme 1. Scheme 1 may be readily applied to the synthesis of other 3-aryl quinolines, as recognized by those skilled in the art.

Scheme 1:

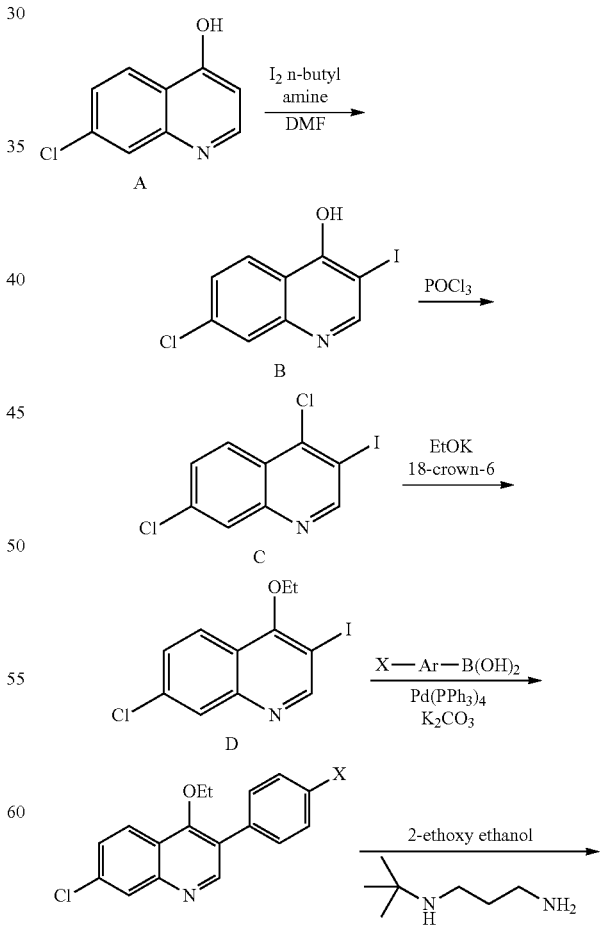

-continued

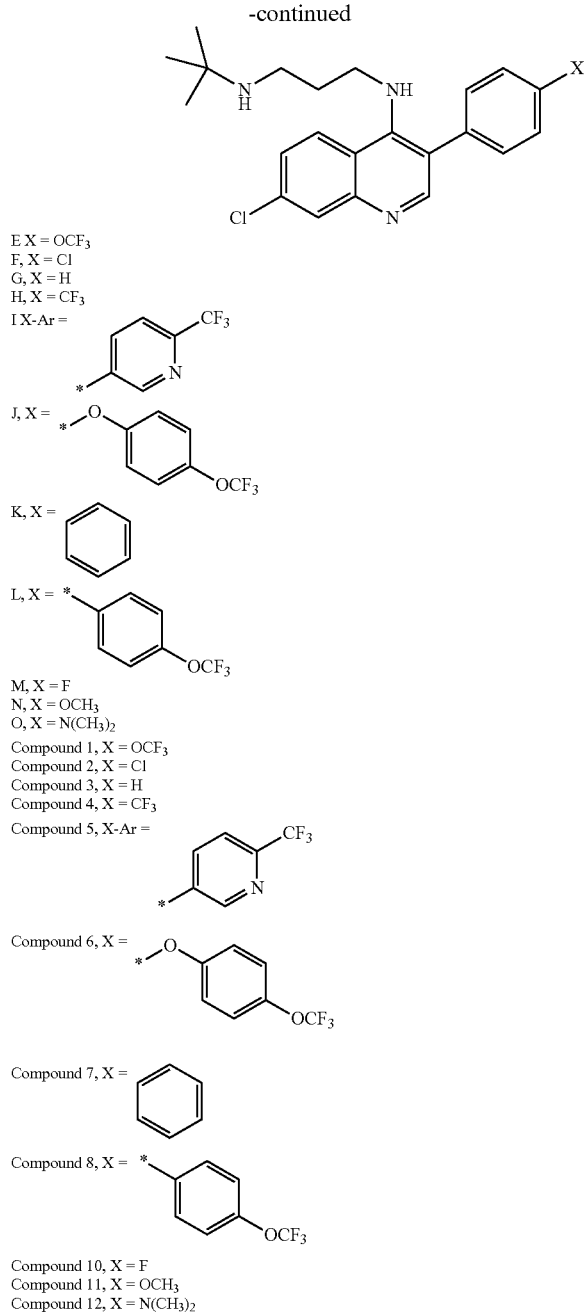

E X = OCF₃
F, X = Cl
G, X = H
H, X = CF₃
I X-Ar =

J, X =

K, X =

L, X =

M, X = F
N, X = OCH₃
O, X = N(CH₃)₂
Compound 1, X = OCF₃
Compound 2, X = Cl
Compound 3, X = H
Compound 4, X = CF₃
Compound 5, X-Ar =

Compound 6, X =

Compound 7, X =

Compound 8, X =

Compound 10, X = F
Compound 11, X = OCH₃
Compound 12, X = N(CH₃)₂

For Scheme 1, N1-(tert-butyl)-N3-(7-chloro-3-(4-(trifluoromethoxy)phenyl)-quinolin-4-yl)-propane-1,3-diamine (Compound 1), is obtained in five steps starting from commercially available 7-chloroquinolin-4-ol (A) with an overall yield of approximately 20%, as outlined in further detail herein.

The first step involves the selective iodination of position 3 of the quinolone nucleus with iodine in the presence of n-butylamine in DMF to give 7-chloro-3-iodoquinolin-4-ol (B) according to the procedure of Hart (Hart, *J Med Chem* 49, 1101-1112 (2006) incorporated by reference herein), in approximately 59% yield. Without further purification, this material is converted cleanly to the corresponding 4,7-dichloro-3-iodoquinoline (C) in approximately 99% yield according to the procedure of Andersag (Andersag, Chem Ber 81, 499-507, (1948), incorporated by reference herein).

The iodoquinoline is then treated in THF with potassium ethoxide in the presence of a catalytic amount of 18-crown-6 ether to give pure 7-chloro-4-ethoxy-3-iodoquinoline (D) in approximately 90% yield as shown, for example, by GC-MS and NMR. In the next step, Suzuki coupling conditions (Mphahlele, *J Chem Res* 2008, 437-440 (2008) incorporated by reference herein) may be used to react 4-(trifluoromethoxy)-phenyl)boronic acid with the iodoquinoline intermediate (D) in the presence of tetrakis(triphenylphosphine)palladium (Pd(PPh3)4) and 2M potassium carbonate in DMF. The reaction is allowed to proceed at 85° C. to give 7-chloro-4-ethoxy-3-(4-(trifluoromethoxy)phenyl)quinoline (E) in approximately 63% yield as white crystalline material after flash chromatography. Finally, the desired compound (Compound 1) is obtained by reacting the 4-ethoxy quinoline derivative (E) with N-tert-butyl propane 1,3 diamine in the presence of phenol according to the procedure of Andersag supra, in a Carius tube using 2 ethoxyethanol as a solvent at 180° C. for 4 days. The crude product is further purified by flash chromatography followed by crystallization in ethyl acetate to give Compound 1 as transparent white rectangular plates in approximately 59% yield.

In certain embodiments, 7-chloro-3-iodoquinolin-4-ol (B) may be synthesized as follows. To a stirred suspension of 7-chloro-quinolone (A) (20.0 gm, 111 mmol) in DMF (100 mL) is added successively n-butylamine (81.2 gm, 1.11 mol), iodine (19.8 gm, 155.6 mmol) and 20 mL of saturated aqueous potassium iodide (KI). Upon the addition of n-butyl amine all of (A) dissolves. The yellow solution is stirred at room temperature for 36 hours. Then 0.1 M sodium thiosulfate (Na2S03, 800 mL, 80 mmol) is added and the solution changes to colorless with formation of white precipitate. This is filtered and the white precipitate is washed with 4×200 ml of water. The white precipitate is allowed to dry on the fritted funnel under vacuum under ambient conditions for 3-4 days to give approximately 20.0 g (approximately 59% yield) of (B) as a white powder. This material may be used without further purification.

For the synthesis of 4,7-dichloro-3-iodoquinoline (C), the following method may be used. A suspension of 7-chloro-3-iodoquinolin-4-ol (B) (10.0 gm, 32.8 mmol) in 30 ml of phosphoryl chloride is heated in an oil bath to reflux. After about 3 hours, all starting material is completely dissolved yielding a dark brown solution, and refluxing is continued for another hour. The solution was then allowed to cool to room temperature and the resulting suspension is poured slowly into a stirred 500 mL beaker of ice. Next NaOH (75 g) is added slowly in small portions while stirring, causing a yellowish precipitate to form. The yellowish precipitate is filtered, washed with water and dried on a fritted funnel under house vacuum suction overnight to give 10.5 g (99% yield) of (C) as a yellowish solid. The product may be pure as shown by TLC (eluent hexane/ethyl acetate 2/8, Rf=0.5), GC-MS and NMR. GC-MS may show one peak with 323 M+, 100%. 1H NMR: 9.11 (1H, s), 8.21 (1H, d, J=9.07 Hz), 8.10 (1H, s), 7.59 (1H, d, J=8.33 Hz).

For the synthesis of 7-chloro-4-ethoxy-3-iodoquinoline (D), the following method may be used. To a stirred solution of (C) (5.00 gm 15.5 mmol) in dry THF (100 mL) is added 18-crown-6 ether (307 mg, 1.2 mmol, 2.5% equivalent relative to potassium ethoxide) and potassium ethoxide (3.90 gm, 46.4 mmol). The resulting yellow suspension is stirred for 1 hour at room temperature. GC-MS may show no more starting material with a clean formation of the desired 7-chloro-4-ethoxy-3-iodoquinoline (D). The suspension is then suction filtered over a layer of silica gel placed inside a fritted funnel and washed with ethyl acetate (3×20 mL).

The cloudy yellow solution is further filtered over celite and rotoevaporated to afford 4.64 gm (approximately 90% yield) of (D) as a white solid. The product may be pure as shown by, for example, thin layer chromatography (TLC) (eluent hexane/ethyl acetate 2/8, Rf=0.6), GC-MS and NMR, and may be used in the next step without further purification. In certain embodiments, GC-MS shows one peak with 333 M+, 76%; 305 (M-Et), 100%. $^1$H NMR: 9.06 (1H, s), 8.07 (1H, d, J=2.06 Hz), 8.02 (1H, d, J=8.93 Hz), 7.51 (1H, dd, J=8.93, 2.07 Hz), 4.26 (2H, q, J=7.02 Hz), 1.60 (4.5H, t, J=7.02, 1.5H residual water).

In certain embodiments, 7-chloro-4-ethoxy-3-(4-(trifluoromethoxy) phenyl)quinoline (E) may be synthesized as follows. A solution containing (D) (333 mg, 1.0 mmol), 4-(4-(trifluoromethoxy)phenyl)boronic acid (309 mg 1.5 mmol), tetrakis(triphenylphosphine)palladium (0) Pd(PPh3)4 (57.8 mg, 0.05 mmol), 2 mL of 2M K2CO3 (4.0 mmol) and DMF (10 mL) is heated at 85° C. under argon for 24 hours. After about 2 hours, the solution turns black. The solution is allowed to cool to room temperature, diluted with ethyl acetate (50 mL), suction filtered over a layer of silica gel placed on top of a thin layer of Celite, to eliminate the palladium catalyst, and washed with an additional 50 mL of ethyl acetate. The combined filtrate is dried over Na2SO4, filtered and roto-evaporated to afford 529 mg of a white solid. This material is suspended in 2-3 ml of CH$_2$Cl$_2$ and the insoluble material is filtered out through Celite. The solution may be purified by flash chromatography using hexane/ethyl acetate 8/2 as eluent to give approximately 232 mg (approximately 63% yield) of (E) as a white crystalline solid. The product may be pure as shown by, for example, TLC (eluent hexane/ethyl acetate 2/8, Rf=0.5) GC-MS and NMR, and may be used in the next step without further purification. GC-MS may show one peak with 367 M+, 75%; 339 (M-Et), 100%. 1H NMR: 8.83 (1H, s), 8.18 (1H, d, J=8.92 Hz), 8.10 (1H, d, J=1.98 Hz), 7.68 (2H, d, J=8.43 Hz), 7.53 (1H, dd, J=8.93, 2.01 Hz), 7.36 (2H, d, J=8.27 Hz), 3.80 (2H, q, J=7.02 Hz), 1.25 (3H, t, J=7.03 Hz).

Compound 1, N1-(tert-butyl)-N3-(7-chloro-3-(4-(trifluoromethoxy)-phenyl)-quinolin-4-yl)propane-1,3-diamine, may be synthesized as follows. A stirred solution of (E) (367 mg, 1.0 mmol), N-tert butyl propane 1,3 diamine (390 mg, 3.0 mmol), phenol (282 mg, 3.0 mmol) and 2-ethoxy ethanol (5 mL) in a Carius tube is placed in an 180° C. oil bath for 4 days. Then it is allowed to cool to room temperature and the contents of the Carius tube are transferred into a round bottom flask and rotoevaporated to dryness. The yellow residue is suspended in 30 mL of CH$_2$Cl$_2$ and 10 mL of 10% NaOH, the small amount of insoluble material may be filtered out. The organic layer is then washed with 10% sodium hydroxide (2×10 mL), brine (10 mL), dried over Na$_2$SO$_4$, filtered and rotoevaporated to afford 506 mg of a yellowish solid. This material may be purified by flash chromatography using (ethyl acetate/triethylamine 9/1)/hexane 50/50 as eluent to give approximately 266 mg (approximately 59% yield) of (Compound 1) as a white crystalline solid. This material is dissolved in ethyl acetate and the solvent is allowed to slowly evaporate in the hood to give transparent white rectangular plates. An x-ray structure of this material may be obtained to confirm its structure. GC-MS may show one peak with 451 M+, 28%; 351 (M-C6H14N), 100%. 1H NMR: 8.37 (1H, s), 8.07 (1H, d, J=9.05 Hz), 7.96 (1H, d, J=2.19 Hz), 7.45-7.44 (2H, m), 7.37 (1H, dd, J=9.00, 2.22 Hz), 7.28 (2H, s) 2.95 (2H, q, J=5.35 Hz), 2.73 (2H, t, J=5.35 Hz), 1.60 (2H, q, J=3.22 Hz) 1.14 (9H, s). Compounds 2, 3, 4, 5, 6, 7, 8, 10, 11 and 12 may be prepared in the similar manner as described for the preparation of compound 1 as shown in Scheme 1.

Alternatively, compound 1 can be synthesized according to Scheme 2 by performing the Suzuki coupling directly on the 4-chloro 3-iodo quinoline (C) using dichloro [1,1' bis (diphenylphosphino)ferrocene)] palladium (II) [PdCl$_2$ (dppf)] (Hayashi, T. *J. Am. Chem. Soc.* 1984, 106, 158-163, incorporated by reference herein) as a catalyst to give 4,7-dichloro-3-(4-(trifluoromethoxy)phenyl)quinoline (P) in 79% yield a white solid after flash chromatography. Finally, the desired product compound 1 is obtained using the same procedure as described in Scheme 2 in approximately 90% yield. In some embodiments, this new and more efficient method (Scheme 2) may give an overall yield of approximately 42%.

Scheme 2:

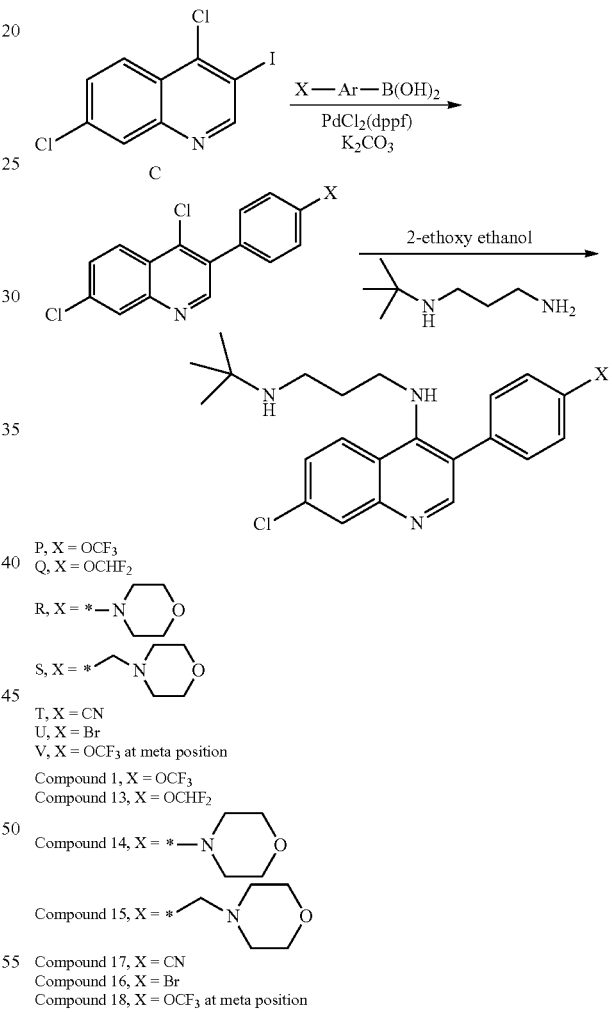

In certain embodiments, with reference to Scheme 2, 4,7-dichloro-3-(4-(trifluoromethoxy) phenyl)quinoline (P) may be synthesized as follows. 4,7-dichloro-3-iodoquinoline (C) (3.23 gm 10.0 mmol) and 4-(4-(trifluoromethoxy) phenyl)boronic acid (2.06 gm, 10.0 mmol) is dissolved in DMF (60 mL) while degassing with argon. To this stirred solution is added 10 mL of 2M K$_2$CO$_3$ (20.0 mmol) resulting in a formation of a white precipitate. Next, dichloro [1,1' bis (diphenylphosphino)ferrocene)] palladium (II) [PdCl$_2$ (dppf)] (366 mg, 0.5 mmol) is added. After degassing for an additional 10 minutes the flask was septum capped and put in an 85° C. oil bath under argon for 3 hrs. GC-MS may show no more starting materials with clean formation of the desired Compound P. The solution is then allowed to cool to room temperature and suction filtered over celite and washed with ethyl acetate (3×100 mL). The combined filtrate is dried over $Na_2SO_4$, filtered and rotoevaporated to dryness yielding a black residue to which is added 300 mL of ethyl acetate. The suspension is stirred vigorously for 30 minutes at room temperature, filtered through celite and rotoevaporated to afford approximately 4.10 gm of brown solid. This material may be purified by flash chromatography using hexane/ethyl acetate 9/1 as eluent to give approximately 2.83 gm (approximately 79% yield) of (P) as a white solid. The product may be pure as shown, for example, by TLC (eluent hexane/ethyl acetate 9/1, Rf=0.48) GC-MS and NMR, and may be used in the next step.

Compound 1, $N_1$-(tert-butyl)-N3-(7-chloro-3-(4-(trifluoromethoxy)phenyl)-quinolin-4-yl)propane-1,3-diamine, may be synthesized as follows. A stirred solution of (P) (357 mg, 1.0 mmol), N-tert butyl propane 1,3 diamine (390 mg, 3.0 mmol), phenol (94 mg, 1.0 mmol) and 2-ethoxy ethanol (3 mL) in a Carius tube is placed in an 150° C. oil bath for 24 hours. GC-MS may show no more starting material with clean formation of the desired product compound 1. Then it is allowed to cool to room temperature and the contents of the Carius tube are transferred into a round bottom flask and rotoevaporated to dryness. The yellow residue is suspended in 30 mL of $CH_2Cl_2$ and 10 mL of 10% NaOH. The organic layer is then washed with 10% sodium hydroxide (2×10 mL), brine (10 mL), dried over $Na_2SO_4$, filtered and rotoevaporated to afford 584 mg of a brownish solid. This material is purified by flash chromatography using (ethyl acetate/triethylamine 9/1)/hexane 50/50 as eluent to give approximately 406 mg (approximately 90% yield) of compound 1 as a white crystalline solid. GC-MS and NMR may be identical to those described herein. Compounds 13, 14, 15, 16, 17, and 18 may also be prepared in a similar manner as described for the preparation of compound 1 as shown in Scheme 2.

In certain embodiments, the synthesis of Compounds 22, 23, 24, 25, and 26 may be accomplished using the reaction conditions described in Scheme 3.

Scheme 3:

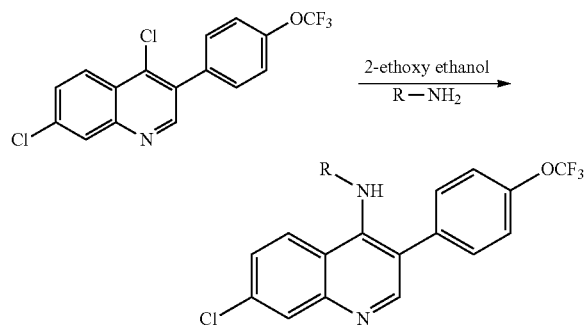

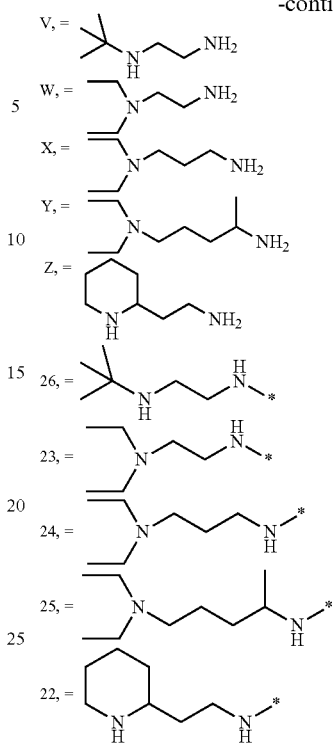

III. Pharmaceutical Compositions

The compounds disclosed herein may be included in pharmaceutical compositions (including therapeutic and prophylactic formulations). Pharmaceutical compositions as described herein include one or more compounds according to the present description. In addition to one or more compounds as described herein, pharmaceutical compositions according to the present disclosure may include one or more additional therapeutic agents, including, for example, one or more additional antimalarial or antiinfective agent, antibiotics, anti-inflammatory agents, or drugs that are used to reduce pruritus, such as an antihistamine. In preparing the pharmaceutical compositions, the one or more compounds as described herein and, optionally, the one or more additional active agents, may be combined together with one or more pharmaceutically acceptable vehicles or carriers. The pharmaceutical compositions described herein may be combined with or used simultaneously with one or more other therapeutic regimens or compositions. Where one or more additional antimalarial or antiinfective agent is included in a pharmaceutical composition according to the present invention, such agent(s) may be selected from, for example, quinolines, such as chloroquine, quinine, and mefloquine; the antifolates, such as pyrimethamine and sulfadoxine; and the anti-respiratory combination of atovaquone and proguanil.

Pharmaceutical compositions according to the present invention may be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In an embodiment, the compound can be administered ex vivo by direct exposure to cells, tissues or organs originating from a subject.

To formulate the pharmaceutical compositions, the one or more compounds may be combined with various pharmaceutically acceptable additives, as well as a base or vehicle for dispersion of the compound. Such additives include, but are not limited to, pH control agents, such as arginine, sodium hydroxide, glycine, hydrochloric acid, and citric acid. In addition, local anesthetics (for example, benzyl alcohol), isotonizing agents (for example, sodium chloride, mannitol, sorbitol), adsorption inhibitors (for example, Tween 80 or medium chain triacylglycerols such as myglyol 812), solubility enhancing agents (for example, cyclodextrins and derivatives thereof), stabilizers (for example, serum albumin), and reducing agents (for example, glutathione) may be included.

Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Mont.) and IL-12 (Genetics Institute, Cambridge, Mass.), among many other suitable adjuvants well known in the art, may be included in the composition. When the composition is a liquid, the tonicity of the formulation, as measured with reference to the tonicity of 0.9% (w/v) physiological saline solution taken as unity, may be adjusted to a value at which no substantial, irreversible tissue damage will be induced at the site of administration. For example, the tonicity of the solution may be adjusted to a value of about 0.3 to about 3.0, such as about 0.5 to about 2.0, or about 0.8 to about 1.7.

In preparing a pharmaceutical composition according to the present description, the one or more compounds may be dispersed in a base or vehicle, which can include a hydrophilic compound having a capacity to disperse the compound, and any additives. The base may be selected from a wide range of suitable compounds, including but not limited to, copolymers of polycarboxylic acids or salts thereof; carboxylic anhydrides (for example, maleic anhydride); with other monomers (for example, methyl(meth)acrylate and acrylic acid); hydrophilic vinyl polymers, such as polyvinyl acetate, polyvinyl alcohol, polyvinylpyrrolidone, cellulose derivatives such as hydroxymethylcellulose and hydroxypropylcellulose; natural polymers, such as chitosan, collagen, sodium alginate, gelatin, hyaluronic acid; and nontoxic metal salts thereof.

A biodegradable polymer may be selected as a base or vehicle, such as, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters and sucrose fatty acid esters may be employed as vehicles. Hydrophilic polymers and other vehicles can be used alone or in combination, and enhanced structural integrity can be imparted to the vehicle by, for example, partial crystallization, ionic bonding, or cross-linking. The vehicle may be provided in a variety of forms, including fluid or viscous solutions, gels, pastes, powders, microspheres, and films for direct application to a mucosal surface.

The one or more compounds may be combined with the base or vehicle according to a variety of methods, and release of the compound may be via diffusion, disintegration of the vehicle, or associated formation of water channels. In some embodiments, the compound may be dispersed in microcapsules (microspheres) or nanoparticles prepared from a suitable polymer, for example, 5-isobutyl-2-cyanoacrylate (see, for example, Michael et al., J. Pharmacy Pharmacol. 43:1-5, 1991), and dispersed in a biocompatible dispersing medium, which may provide sustained delivery and biological activity over a protracted time. Alternatively, the one or more compounds may be combined with a mesoporous silica nanoparticle, such as a mesoporous silica nanoparticle complex with one or more polymers conjugated to its outer surface.

In certain embodiments, the pharmaceutical compositions of the disclosure may contain as pharmaceutically acceptable vehicles, substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, and triethanolamine oleate.

For solid compositions, conventional nontoxic pharmaceutically acceptable vehicles may be used which include, for example, pharmaceutical grades of mannitol, lactose, starch, magnesium stearate, sodium saccharin, talcum, cellulose, glucose, sucrose, and magnesium carbonate.

Pharmaceutical compositions for administering the one or more compounds may also be formulated as a solution, microemulsion, or other ordered structure suitable for a high concentration of active ingredients. The vehicle may be a solvent or dispersion medium containing, for example, water, ethanol, polyol (for example, glycerol, propylene glycol, and liquid polyethylene glycol), and suitable mixtures thereof. Proper fluidity for solutions may be maintained, for example, by the use of a coating such as lecithin, by the maintenance of a desired particle size in the case of dispersible formulations, and by the use of surfactants.

In an embodiment, it may be desirable to include isotonic agents, for example, sugars, polyalcohols such as mannitol and sorbitol, or sodium chloride in the composition. Prolonged absorption of the one or more compounds may be obtained by including in the composition an agent which delays absorption, for example, monostearate salts and gelatin.

In certain embodiments, the one or more compounds may be administered in a time release formulation, for example in a composition which includes a slow release polymer. These compositions may be prepared with vehicles that will protect against rapid release, for example, a controlled release vehicle such as a polymer, microencapsulated delivery system or bioadhesive gel. Controlled release binders suitable for use in accordance with the disclosure include any biocompatible controlled release material which is inert to the active agent and which is capable of incorporating the compound and/or other biologically active agent. Numerous such materials are known in the art. Controlled-release binders may be materials that are metabolized slowly under physiological conditions following their delivery (for example, at a mucosal surface, or in the presence of bodily fluids).

Exemplary binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, or inflammation. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity.

Exemplary polymers include polyglycolic acids and polylactic acids, poly(DL-lactic acid-co-glycolic acid), poly(D-lactic acid-co-glycolic acid), and poly(L-lactic acid-coglycolic acid). Other useful biodegradable or bioerodable polymers include, but are not limited to, poly(epsilon-caprolactone), poly(epsilon-caprolactone-CO-lactic acid), poly(epsilon-caprolactone-CO-glycolic acid), poly(beta-hydroxy butyric acid), poly(alkyl-2-cyanoacrylate), hydrogels such as poly(hydroxyethyl methacrylate), polyamides, poly(amino acids) such as L-leucine, glutamic acid, L-aspartic acid, poly(ester urea), poly(2-hydroxyethyl DL-aspartamide), polyacetal polymers, polyorthoesters, polycarbonate, polymaleamides, polysaccharides, and copolymers thereof.

Methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Dispersions may be prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, and thimerosal.

IV. Methods of Treatment

The compounds and pharmaceutical compositions disclosed herein may be used for treating, inhibiting or preventing parasitic diseases, such as malaria, caused by organisms such as *Plasmodium* sp., including *Plasmodium falciparum*. Other examples of human or animal parasitic diseases that may be treated using the compounds and pharmaceutical compositions disclosed herein include toxoplasmosis, amebiasis, giardiasis, leishmaniasis, trypanosomiasis, coccidiosis, and schistosomiasis, caused by organisms such as *Toxoplasma* sp., *Eimeria* sp., *Babesia* sp, *Theileria* sp. Additional parasites that cause malaria include *Plasmodium vivax, Plasmodium ovale, Plasmodium knowlesi, Plasmodium malariae, Plasmodium yoelii,* and *Plasmodium berghei.*

In particular embodiments, the compounds and compositions disclosed herein may be administered to a subject to prevent or inhibit drug-resistant malaria such as chloroquine-resistant malaria or multidrug-resistant malaria that is caused by organisms harboring resistance to chloroquine, quinine, mefloquine, pyrimethamine, dapsone, atovaquone, or any other available anti-malarial drug.

Without being bound by a particular theory, it is presently believed that the compounds disclosed herein can pi-pi stack onto the heterocyclic aromatic nucleus of heme, which may be indicative of their mechanism of action against malaria.

One embodiment disclosed herein includes administering at least one of the compounds disclosed herein to a subject determined to be in need of treatment for multidrug-resistant malaria.

In further embodiments, the compounds and pharmaceutical compositions disclosed herein may be coadministered with another pharmaceutically active compound. For example, the compounds may be coadministered with quinine, chloroquine, atovaquone, proguanil, primaquine, amodiaquine, mefloquine, piperaquine, artemisinin, artesunate, endoperoxidases, methylene blue, pyrimethamine, sulfadoxine, artemether-lumefantrine (Coartem®), dapsone-chlorproguanil (LAPDAP®), artesunate, quinidine, clopidol, pyridine/pyridinol analogs, 4(1H)-quinolone analogs, dihydroartemisinin, a mixture of atovaquone, proguanil, an endoperoxide, an acridone as disclosed in WO 2008/064011, another 3-aryl quinoline as disclosed in WO 2010/059633, or any combination or mixtures of these, whether administered separately or in a single pharmaceutical composition.

In accordance with the various treatment methods of the disclosure, the compound may be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compounds, compositions and methods of the present disclosure include humans, as well as non-human primates and other animals such as companion animals, livestock animals, animals used in models of parasitic infection, or animals used in pharmaceutical testing, such as pharmacokinetics and toxicological testing, including mice, rats, rabbits, and guinea pigs. To identify subjects for prophylaxis or treatment according to the methods of the disclosure, accepted screening methods are employed to determine risk factors associated with a parasitic infection to determine the status of an existing disease or condition in a subject. These screening methods include, for example, preparation of a blood smear from an individual suspected of having malaria. The blood smear is then fixed in methanol and stained with Giemsa and examined microscopically for the presence of *Plasmodium* infected red blood cells. These and other routine methods allow a clinician to select patients in need of therapy using the methods and pharmaceutical compositions of the disclosure.

The administration of the disclosed compounds and pharmaceutical compositions may be for prophylactic or therapeutic purposes. When provided prophylactically, the compound is administered to a subject in advance of a symptom. The prophylactic administration of the compound serves to prevent or ameliorate subsequent disease process. When provided therapeutically, the compound is administered to a subject at or after the onset of a symptom of disease or infection.

For prophylactic and therapeutic purposes, the compound or pharmaceutical composition may be administered to the subject orally or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound may be provided as repeated doses within a prolonged prophylaxis or treatment regimen to yield clinically significant results to alleviate one or more symptoms or detectable conditions associated with a targeted disease or condition as set forth herein.

Determination of effective dosages in this context may be based on animal model studies followed up by human clinical trials and may be guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages may be determined using in vitro models (for example, immunologic and histopathologic assays). Using such models, calculations and adjustments may be required to determine an appropriate concentration and dose to administer a therapeutically effective amount of the compound (for example, amounts that are effective to elicit a desired immune response or alleviate one or more symptoms of a targeted disease). In certain embodiments, an effective amount or effective dose of the compound may simply inhibit or enhance one or more selected biological activities correlated with a disease or condition, as set forth herein, for either therapeutic or diagnostic purposes.

The actual dosage of the compound may vary according to factors such as the disease indication and particular status of the subject (for example, the subject's age, size, fitness, extent of symptoms, and susceptibility factors), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response.

A therapeutically effective amount may be one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and compositions of the disclosure is about 0.01 mg/kg body weight to about 100 mg/kg body weight, such as about 0.05 mg/kg to about 50 mg/kg body weight, or about 0.5 mg/kg to about 5 mg/kg body weight.

The dosage may be varied to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder or sustained release oral versus injected particulate or transdermal delivery formulations.

The instant disclosure also includes kits, packages and multi-container units containing the herein described pharmaceutical compositions, active ingredients, and/or devices and consumables that facilitate the administration the same for use in the prevention and treatment of diseases and other conditions in mammalian subjects.

In an embodiment, the compound may be formulated in a pharmaceutical composition for delivery to a subject. In such embodiments, pharmaceutical compositions according to the present description may be used. The compound or composition within which it is formulated may be contained in a bulk dispensing container or unit or multiunit dosage form. Optional dispensers can be provided, for example, a pulmonary or intranasal spray applicator. Packaging materials optionally include a label or instruction indicating for what treatment purposes and/or in what manner the pharmaceutical agent packaged therewith can be used.

In an embodiment, the method of treating a *Plasmodium* infection comprises administering a therapeutically effective amount of a compound. The compound may be administered orally, subcutaneously, intravenously, or intramuscularly to a subject suffering from or at risk of suffering from a *Plasmodium* infection. In an embodiment, the *Plasmodium* infection may be an infection with a *Plasmodium* strain resistant to one or more of the following classes of compounds: quinine, mefloquine, chloroquine, or atovaquone.

The specific examples included herein are for illustrative purposes only and are not to be considered as limiting to this disclosure. Any active agents and reagents used in the following examples are either commercially available or can be prepared according to standard literature procedures by those skilled in the art of organic synthesis. In light of this disclosure, those of skill in the art will recognize that variations of these examples and other examples of the disclosed method would be possible without undue experimentation.

EXAMPLE 1

The In Vitro Efficacy of Exemplary Compounds

Table 1 shows the antiplasmiodial $IC_{50}$ values (nM) of several antimalarial agents, in comparison to certain compounds disclosed herein, when used against selected *P. falciparum* strains. The D6 strain of *P. falciparum* is sensitive to the antiplasmodial action of chloroquine, but strains Dd2, Tm90.C2B (not shown), and 7G8 are all resistant to chloroquine and are all multidrug resistant strains. The Dd2 and Tm90.C2B strains also exhibit a high level of resistance to quinine and mefloquine, while Tm90.C2B is also resistant to atovaquone.

The $IC_{50}$ values listed in Table 1 were determined by the fluorescence-based SyBr Green assay described in Smilkstein (Smilkstein M, Antimicrob Agents Chemother 48, 1803-1806 (2004)). Values are the mean of at least two experiments, each performed in triplicate. Values did not vary by greater than 15% between experiments. NT=not tested.

TABLE 1

| | $IC_{50}$ Values (nM) | | |
|---|---|---|---|
| Antimalarial Compound | Strain D6 | Strain Dd2 | Strain 7G8 |
| Chloroquine | 9.2 | 120 | 78 |
| Quinine | 19 | 87 | 30 |
| Quinacrine | 5 | 10 | 9 |
| Atovaquone | 0.1 | 0.1 | 0.1 |
| Sontochin | 8 | 19 | 20 |
| Compound 1 | 0.9 | 1.4 | 1.3 |
| Compound 2 | 8 | 15 | 5.8 |
| Compound 3 | 8.7 | 17 | 6.4 |
| Compound 4 | 4.8 | 11.9 | 9.7 |
| Compound 5 | 55.2 | 89 | 132 |
| Compound 6 | 2.3 | 3.3 | 1.6 |
| Compound 7 | 0.9 | 2.9 | 1.4 |
| Compound 8 | 5.3 | 5.9 | 8.3 |
| Compound 10 | 13.1 | 11.7 | 32.8 |

TABLE 1-continued

| Antimalarial Compound | IC$_{50}$ Values (nM) | | |
|---|---|---|---|
| | Strain D6 | Strain Dd2 | Strain 7G8 |
| Compound 11 | 9.5 | 11.7 | 20.6 |
| Compound 12 | 5.1 | 7.0 | 11.7 |
| Compound 13 | 2.4 | 4.9 | 5.6 |
| Compound 14 | 4.4 | 6.7 | 8.2 |
| Compound 15 | 0.8 | 0.9 | 0.9 |
| Compound 16 | <2.5 | <2.5 | 2.5 |
| Compound 17 | 13.5 | 21.8 | 26.3 |
| Compound 18 | <2.5 | <2.5 | <2.5 |
| Compound 19 | NT | NT | NT |
| Compound 20 | NT | NT | NT |
| Compound 21 | NT | NT | NT |
| Compound 22 | 0.7 | 1.8 | <2.5 |
| Compound 23 | 35 | 80 | 93 |
| Compound 24 | 3.4 | 4.4 | 8.5 |
| Compound 25 | 3.5 | 7.8 | 11.1 |
| Compound 26 | 0.6 | 4.9 | 4.5 |

It is evident from the results that Sontochin, which differs from chloroquine only in the 3-position methyl group, retains activity against the drug resistant strains of *P. falciparum* with IC$_{50}$ values ranging from 8 to 20 nM.

An aryl substituent at the 3-position was added to the 3-aryl quinonline core to evaluate the effect of such a substitution on intrinsic antiplasmodial activity. Without being bound by theory, this concept evaluated the hypothesis that a large metabolically stable group might further impede interaction with the resistance-mediating pfcrt efflux pump and also may help to guide the drug into the lipid droplets where hemozoin is formed in the parasite's digestive vacuole (Pisciotta J M, et al, Biochem J 402, 197-204, (2007)).

The compounds described in Table 1 all have an aryl substituent at the 3-position. As shown in Table 1, many of these compounds exhibit enhanced anitplasmodial activity against the tested strains relative to sontochin.

Short chain analogs of Sontochin exhibit equal to superior antiplasmodial activity compared to Sontochin and equal potency against multidrug-resistant strains of *P. falciparum*. A tert-butyl moiety incorporated into the terminal amine group of the 4-aminoquinoline side chain, in order to affect metabolic stability, was found to also enhance intrinsic antiparasitic activity by ≈2-fold over analogs containing a diethylamine terminal group. Generally, the data in Table 1 indicates that aryl substituents at the 3-position of the quinoline core endow the compounds with enhanced in vitro antiplasmodial activity.

Furthermore, Compound 1 was evaluated against the strain Tm90.C2B. With that strain, it displayed an IC$_{50}$ value of 1.3, a marked improvement relative to chloroquine (106.2), quinine (96), atovaqone (7700), and sontochin (19.1).

EXAMPLE 2

In Vivo Potency of Compound 1

The efficacy of Compound 1 in vivo using a *P. yoelii* mouse model of malaria (Strain K model) was studied. Female CF1 mice were inoculated intravenously with 1-2 million infected red blood cells obtained from infected donor animals. Infected cells were collected then randomly sorted into groups of four mice on Day 0. Drug administration began on Day 1. Dosages ranged from 1 to 64 mg/kg/day and included a no drug control and a chloroquine positive control. Both drugs were dissolved in water and administered as salts; chloroquine as the phosphate salt and Compound 1 as the HCl salt. Both drugs were administered daily by gavage as the dihydrochloride salt dissolved in 100 μl of water for Days, 1, 2, 3, and 4. Blood films were prepared on Day 5 (the day after the final drug dose), fixed in methanol, stained with Giemsa, and viewed microscopically to assess parasitemia.

Treatment with Compound 1 yielded an ED$_{50}$ value of 0.25 mg/kg/day whereas chloroquine had an ED$_{50}$ of 1.5 mg/kg/day. Compound 1 displayed a stronger cure rate relative to chloroquine. While chloroquine treatment did not cure any of the animals at dosages as high as 64 mg/kg/day (consistent with a long history of use of this model system), Compound 1 cured all animals at 16 and 64 mg/kg/day. Thus, the non-recrudescence dose of Compound 1 is less than or equal to 16/mg/kg/day in this system.

Table 2 summarizes the in vitro and in vivo activities of Compound 1.

TABLE 2

| | Avg IC$_{50}$ values vs P. falciparum strains | Cytotoxicity: IC$_{50}$ vs. murine splenic lymphocytes | IVTI | In vivo efficacy vs. P. yoelii/ CF1 mice: ED$_{50}$ (NRD) |
|---|---|---|---|---|
| Compound 1 | 1.2 nM | 4980 nM | 4150 | 0.25 mg/kg/day ≤16 mg/kg/day |

IVTI = In vitro Therapeutic Index (ratio of IC$_{50}$'s murine splenic lymphocytes/*P. falciparum* strains).
NRD = non-recrudescence dose for all animals in the treatment group.

EXAMPLE 3

Inhibition of hERG Channel by Compound 1

Several antimalarial drugs, including halofantrine, are known to produce a QT interval prolongation via a blockade of the rapidly activating delayed rectifier K+current (IKr), encoded by the human-ether-a-go-go-related gene (hERG) (Traebert M et al, *Eur J Pharmacol* 484, 41-48 (2004)). Thus, it is important to consider hERG channel inhibition for down-selection of 3-aryl quionolines. The inhibitory effects of Compound 1 on the hERG potassium channel current expressed in mammalian cells were evaluated at room temperature using the QPatch HT® (Sophion Bioscience A/S, Denmark), an automatic parallel patch clamp system by ChanTest.

Compound 1 was evaluated at 1 μM, 4 μM, and 12 μM concentrations in duplicate with controls. Compound 1 inhibits hERG channel activity in a concentration dependent manner yielding an IC$_{50}$ of 4.0 μM. For comparison, chloroquine (2.5 μM), mefloquine (2.6 μM), and halofantrine (0.04 μM) are cited as well (Traebert, et al., supra).

Thus, the proarrhythmic risk of Compound 1 was shown to be lower than other antimalarial agents based on the improved cardiac safety index. This result, combined with the antimalarial potency of Compound 1 suggests that an effective dose of Compound 1 carries a lower risk of side effects than currently available antimalarials.

EXAMPLE 4

Cell-Free Assessment of Compound 1 and Potency of 3-Aryl Quinoline Analogs

The binding affinity of Compound 1 and heme in solution was assessed as described by Kelly (Kelly, J X et al, Antimicrob Agents Chemother 46, 144-150 (2002); Kelly J X et al, Mol Biochem Parasitol 123, 47-54 (2002)). This assay correlates heme binding affinity and the mode of binding (i.e., binding to heme monomer or dimer) to intrinsic antimalarial activity in vitro and in vivo.

Association constants for heme-drug complexes were determined with all titrations conducted under aqueous conditions in 20 mM phosphate buffer, at pH 7.0 and 25° C. Titrations with compounds were performed by successive addition of aliquots of a 1 mM stock solution to a 10 µM heme solution at constant pH. All UV/visible spectral data was analyzed digitally with absorbance readings and concentrations corrected for dilution effects. The resulting titration curves were analyzed with Hill plot (Cantor and Schimmel, *Biophysical Chemistry*, W H Freeman and Co, New York, 1980) and non-linear curve fitting methods (Connors, *Chemical Kinetics*, VCH Publishers, New York, 1990). Titration curves were fit to the most accurate binding isotherm and stoichiometry.

Heme:drug interaction was assessed by NMR. NMR investigations involving Compound 1 binding to heme were performed as described in Kelly (Kelly, et al, supra). Using these analyses, Compound 1 was shown to have a strong affinity for free heme.

EXAMPLE 5

In Vitro Screening of 3-Aryl Quinolines

Screening of 3-aryl quinolines is carried out using the SyBr Green Fluorescence-based assay disclosed by Smilkstein (Smilkstein M, Antimicrob Agents Chemother 48, 1803-1806 (2004)). $IC_{50}$ values are determined for each drug in serum-free medium containing ALBUMAX II. Red blood cells are available commercially. Examples of strains to be used in the evaluation include: one or more chloroquine sensitive strains such as D6, 3D7, and 106/1 and one or more drug resistant strains such as Dd2, 7G8, K1, V1/S, Tm90-C2B, FCR3 or FCR1.

Toxicity of candidate molecules is assessed by adding serial dilutions of each 3-aryl quinoline across a 96 well plate containing human HEK cells. After an incubation period (such as 72 hours), cellular proliferation is determined using Alamar Blue. In this assay, cellular proliferation induces chemical reduction of the dye resulting in a color change that is detected spectrophotometrically with a plate reader. Toxicity associated with a candidate molecule would result in the inhibition of cell proliferation.

After determination of in vitro $IC_{50}$ values for each drug against *P. falciparum* and against the human cell line, the ratio of the $IC_{50}$ with the cell line/$IC_{50}$ vs. parasites is used to generate an in vitro therapeutic index (IVTI) for each compound. Compounds that elicit severe toxic effects against HEK cells at submicromolar concentrations may not have strong clinical potential.

Additionally, isobolar experiments are used to assess pharmacologic interactions between a selected analog, e.g., Compound 1, and other drugs. Such a method is described in Kelly J X et al, *Nature* 459, 270-273 (2009).

EXAMPLE 6

In Vivo Testing of 3-Aryl Quinolines

In vivo testing of Compound 1 and other 3-aryl quinolines is performed using any of a number of species of rodent malaria. For example, two such models include *P. yoelii* (K) and *P. berghei* (ANKA gfp+). These two species have been used in evaluation of new antimalarial agents. Additionally strains of each species are available that are susceptible and resistant to chloroquine and other antimalarial drugs. The *P. berghei* GFP transfectant facilitates fluorescence-based determination of parasite burden through fluorescence activated cell sorting (FACS). In addition to the determination of parasitemia, observations of animal weight, activity, grooming and gross examination are recorded, as well as additional toxicity assessment as described. $ED_{50}$ and $ED_{90}$ values are defined as the doses required to reduce parasitemia by 50% and 90%, respectively, relative to controls.

In vivo testing is based on a 4-day suppression model described by Childs (Childs G E, *Ann Trop Med Parasitol* 78, 13-20 (1984). Such a test monitors the suppression of patent infection in female CF1 mice (≈20 gm). Mice are inoculated with parasitized erythrocytes ($2 \times 10_6$) obtained from a donor animal on the first day of the experiment (D0). After 24-48 hours, or when the parasitemia has reached ≈1%, the compounds are administered by gavage at daily intervals for 4 successive days.

Initial doses can include 1 mg/kg, 2 mg/kg, 4 mg/kg, 16 mg/kg, and 64 mg/kg and a vehicle only (negative) control, though other doses can also be tested. After four days of drug treatment, the animals are weighed and blood samples collected. Blood samples are assayed for parasite burden beginning on Day 5 (one day following the last drug treatment). Parasite burden is determined by FACS analysis of *P. berghei*-GFP transfectants, with stained smears for confirmation and/or by direct microscopic analysis of Giemsa-stained blood smears. Drug activity will be expressed as the percent suppression of parasite burden relative to drug-free controls.

Animals observed to be cleared of parasites are observed daily with assessment of parasitemia performed weekly until day 30. If no parasitemia is observed after that point, the animals are scored as cured. Animals with observable parasitemia following 30 days will be euthanized. A tighter range of dosages to more accurately determine the $ED_{50}$ and $ED_{90}$ values for each compound can be performed in a later experiment. Later experiments may also test the effectiveness of various routes of administration. In vivo, the $ED_{50}$ is the dosage of drug required to achieve a 50% reduction in parasitemia while the $ED_{90}$ is the dosage of drug required to achieve a 90% reduction in parsitemia. Non-linear regression analysis can be used to determine $ED_{50}$ (and $ED_{90}$) from the accumulated data as well as the Non-Recrudescence Dose (NRD). Combinations of 3-aryl quinolines with other drugs such as experimental antimalarials (for example, ELQ-300 or dual functional acridones such as T3.5) and more standard antimalarials (for example, artesunate, quinine, and atovaquone) may be assessed in a similar manner. In vivo drug combination studies may be carried out by fixed ratio analysis as described by Kelly (Kelly, et al., 2009 supra).

Without further elaboration, it is believed that one skilled in the art can use the description provided herein to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated. The scope of the invention is therefore defined by the following claims.

The invention claimed is:

1. A compound with the structure of Formula (II)

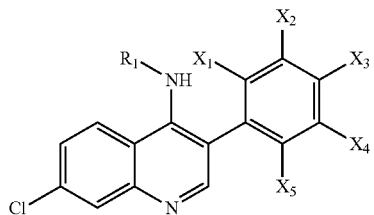

wherein $X_1$, $X_2$, $X_3$, $X_4$, and $X_5$ are independently selected from of H, halo, alkoxy, ether, alkyl, substituted alkyl, alkyl ether, haloalkyl, haloalkyl ether, aryl, substituted aryl, aryl ether, substituted aryl ether, aryl amine, 5-member heterocycle, 6-member heterocycle, amino, benzylic amide, cyano, morpholinyl, N-ethyl morpholinyl, or carboxyl; and $R_1$ is selected from N—N-diethylpropanamino, N-isobutylpropanamino, N-isobutylpropanamino, N—N-diethylpropanamino, and 2-(2-piperidinyl) ethyl; or $R_1$ is N—N-diethyl-(4-methyl) butanamino and $X_3$ is $OCF_3$.

2. The compound of claim 1 wherein the compound has a structure selected from:

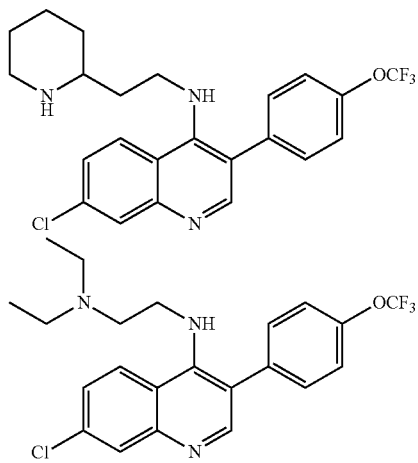

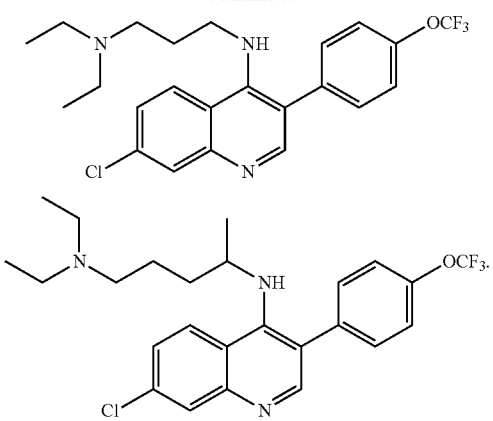

3. A pharmaceutical composition comprising an effective amount of the compound of claim 1.

4. A method of treating a parasitic infection in a subject, the method comprising: administering a therapeutically effective amount of the pharmaceutical composition of claim 3 to the subject.

5. The method of claim 4 wherein the pharmaceutical composition is administered orally, subcutaneously, intravenously or intramuscularly.

6. The method of claim 4 wherein the parasitic infection is a Plasmodium infection.

7. The method of claim 6 wherein the Plasmodium infection comprises an infection with a plasmodium strain resistant to one or more of the following classes of compounds: quinine, mefloquine, chloroquine, or atovaquone.

8. The method of claim 6 wherein the Plasmodium strain is selected from *P. falciparum* and *P. vivax*.

9. The compound of claim 1, wherein $X_1$, $X_2$, $X_4$, and $X_5$ are H and $X_3$ is $OCF_3$.

* * * * *